(12) United States Patent
Obi et al.

(10) Patent No.: US 10,138,454 B2
(45) Date of Patent: Nov. 27, 2018

(54) CULTURE CONTAINER

(71) Applicant: NISSHA PRINTING CO., LTD., Kyoto-shi, Kyoto (JP)

(72) Inventors: Naoko Obi, Kyoto (JP); Atsushi Onishi, Kyoto (JP); Toshihiro Iga, Kyoto (JP)

(73) Assignee: NISSHA PRINTING CO., LTD., Kyoto (JP)

( * ) Notice: Subject to any disclaimer, the term of this patent is extended or adjusted under 35 U.S.C. 154(b) by 0 days.

(21) Appl. No.: 15/122,906

(22) PCT Filed: Jun. 10, 2015

(86) PCT No.: PCT/JP2015/066767
§ 371 (c)(1),
(2) Date: Aug. 31, 2016

(87) PCT Pub. No.: WO2015/198866
PCT Pub. Date: Dec. 30, 2015

(65) Prior Publication Data
US 2017/0067006 A1    Mar. 9, 2017

(30) Foreign Application Priority Data

Jun. 24, 2014 (JP) ................................. 2014-129567
Sep. 5, 2014 (JP) ................................. 2014-181097

(51) Int. Cl.
*C12M 3/00* (2006.01)
*C12M 1/00* (2006.01)
*C12M 1/32* (2006.01)

(52) U.S. Cl.
CPC ............ *C12M 29/20* (2013.01); *C12M 23/12* (2013.01); *C12M 23/38* (2013.01)

(58) Field of Classification Search
CPC ...... C12M 23/12; C12M 23/38; C12M 29/20; B01L 3/50853; B01L 2200/0684;
(Continued)

(56) References Cited

U.S. PATENT DOCUMENTS 4,321,330 A    3/1982  Baker et al.
6,468,788 B1*  10/2002 Marotzki ............... C12M 23/10
                                                   435/288.3
(Continued)

FOREIGN PATENT DOCUMENTS

CN    102015997 A    4/2011
CN    103119151 A    5/2013
(Continued)

OTHER PUBLICATIONS

International Search Report in PCT/JP2015/066767 dated Sep. 8, 2015.
(Continued)

*Primary Examiner* — William H. Beisner

(57) ABSTRACT

A cell-culture container includes a container main body and a presser member. The container main body has a recessed part for containing a cell-culture solution. The presser member is a member that is removably fitted onto an upper side of the recessed part. The presser member has a lower surface, which makes contact with an upper surface of the cell-culture solution in a fitted state, and a bubble-discharge part, which enables the discharge of bubbles in the cell-culture solution to the exterior. Such an arrangement enables accurate observation by the elimination of a meniscus in a culture container.

8 Claims, 18 Drawing Sheets

(58) Field of Classification Search
CPC ......... B01L 2300/042; B01L 2300/048; B01L 2300/0893
See application file for complete search history.

(56) References Cited

U.S. PATENT DOCUMENTS

| | | | |
|---|---|---|---|
| 2006/0234370 A1* | 10/2006 | Korpinen | B01L 3/50853 435/287.2 |
| 2006/0263875 A1 | 11/2006 | Scott et al. | |
| 2008/0207465 A1* | 8/2008 | Ravkin | B01L 3/5085 506/9 |
| 2009/0272748 A1 | 11/2009 | Welch et al. | |
| 2010/0112690 A1* | 5/2010 | Eddington | C12M 23/12 435/374 |
| 2010/0136671 A1 | 6/2010 | Ogihara et al. | |
| 2013/0136657 A1* | 5/2013 | Hofmann | B01L 3/502707 422/68.1 |
| 2013/0203159 A1 | 8/2013 | Itoh et al. | |

FOREIGN PATENT DOCUMENTS

| | | |
|---|---|---|
| EP | 2274413 B1 | 7/2017 |
| JP | S63-186298 A | 11/1988 |
| JP | H05-181068 A | 7/1993 |
| JP | 2006-023644 A | 1/2006 |
| JP | 2006-320323 A | 11/2006 |
| JP | 2010-527582 A | 8/2010 |
| JP | 2014-079227 A | 5/2014 |
| WO | 02087763 A1 | 11/2002 |
| WO | 2010087987 A1 | 8/2010 |

OTHER PUBLICATIONS

Extended Search Report in the corresponding European Patent Application No. 15811969.3 dated Mar. 7, 2017.

* cited by examiner

CULTURE CONTAINER

CROSS-REFERENCE TO RELATED APPLICATIONS

This U.S. National stage application claims priority under 35 U.S.C. § 119(a) to Japanese Patent Application No. 2014-129567, filed in Japan on Jun. 24, 2014, and to Japanese Patent Application No. 2014-181097, filed in Japan on Sep. 5, 2014, the entire contents of Japanese Patent Application Nos. 2014-129567 and 2014-181097 are hereby incorporated herein by reference.

BACKGROUND

Field of the Invention

The present invention relates to a culture container, particularly a culture container used in observation via a microscope and that contains a culture solution.

Background Art

Cultures of cells, bacteria, and the like are widely performed in the fields of medicine and biology. In addition, to cultivate a culture using a container suited to the purpose, culture containers of various shapes and sizes have been developed.

However, if the inner diameter of a recessed part of the container that contains the culture solution is, for example, less than or equal to 16.5 mm, then a phenomenon (hereinbelow, a meniscus), wherein the liquid surface of the culture solution in the container bends due to surface tension, causes a problem in the observation via the microscope. That is, when cells, bacteria, and the like are being observed via an optical microscope, the image adversely degrades due to the lens effect caused by the meniscus. Consequently, observation outside of the center part of the recessed part becomes difficult.

To solve this problem, in a cell-culture container described in Japanese Unexamined Patent Application Publication No. H05-181068, a meniscus-control plate is arranged to float in the container.

SUMMARY

In the cell-culture container described in Japanese Unexamined Patent Application Publication No. H05-181068, there are actually many technical problems, such as in the design, removal, etc. of the meniscus-control plate, and consequently this cell-culture container is not practical.

An object of the present invention is to enable, by the removal of a meniscus in a culture container, accurate observation.

Aspects of the present invention are explained below as the technical solution. These aspects can be arbitrarily combined as needed.

A culture container according to one aspect of the present invention includes a container main body and a presser member.

The container main body has a recessed part for containing a culture solution.

The presser member is a member that is removably fitted onto an upper side of the recessed part. The presser member has a lower surface that makes contact with an upper surface of the culture solution in a fitted state, and a bubble-discharge part that enables the discharge of bubbles in the culture solution to the exterior.

In the container, the presser member is fitted onto the upper side of the recessed part in the state wherein the culture solution is contained in the recessed part of the container main body. Thus, the meniscus is eliminated by the lower surface of the presser member, which makes contact with the upper surface of the culture solution. In this state, bubbles in the culture solution are discharged to the exterior via the bubble-discharge part of the presser member. As a result, the cells in the culture container can be accurately observed.

The lower surface of the presser member may have, at least partially, a tilted surface for guiding bubbles in the culture solution toward the bubble-discharge part. In this container, bubbles in the culture solution are guided to the bubble-discharge part by the tilted surface of the lower surface of the presser member. Accordingly, bubbles tend not to be retained in the vicinity of the lower surface of the presser member.

The lower surface of the presser member may be subject, at least partially, to a hydrophilization treatment.

In this container, the bubbles tend not to be retained in the vicinity of the lower surface of the presser member.

The presser member may further include a liquid-supply part. The liquid-supply part is used to inject a liquid into the culture solution so as to move bubbles in the culture solution toward the bubble-discharge part.

In this container, when the liquid is injected into the culture solution via the liquid-supply part, it causes the bubbles in the culture solution to move toward the bubble-discharge part. Accordingly, bubbles tend not to be retained in the vicinity of the lower surface of the presser member.

A bottom part of the recessed part may have a first portion on which a plurality of microwells is formed. In that case, the lower surface of the presser member makes contact with the upper surface of the culture solution.

The prevention of a meniscus makes it possible to accurately observe the spheroids that are grown in the plurality of microwells.

The bottom part of the recessed part may have a second portion on which the plurality of microwells is not formed. In that case, the bubble-discharge part of the presser member is provided so as to correspond to the second portion.

Because the bubble-discharge part is not formed at a position corresponding to the plurality of microwells in the bottom part, the spheroids that have grown in the plurality of microwells can be observed accurately.

Advantageous Effects

The culture container according to the present invention removes a meniscus and thereby enables accurate observation.

DESCRIPTION OF EMBODIMENTS

1. First Embodiment (1) Overall Structure

A cell-culture container 1, which serves as a culture container according to one embodiment of the present invention, will be explained, with reference to FIG. 1 to FIG. 3.

Figure 1:
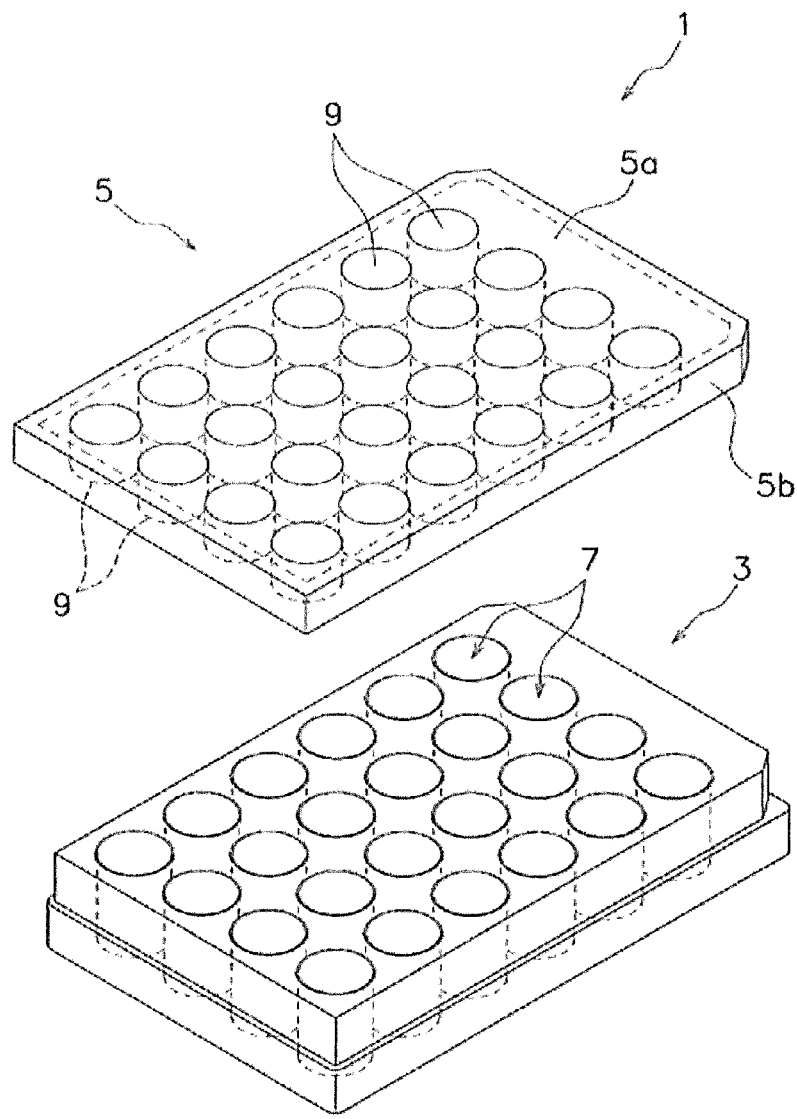
FIG. 1 is an oblique view of a container main body of a cell-culture container.

FIG. 1 is an oblique view of a container main body of a cell-culture container. FIG. 2 and FIG. 3 are oblique views of a presser-member-attached plate of the cell-culture container.

As shown in the figures, the cell-culture container 1 includes a container main body 3 and a presser-member-attached plate 5. The container main body 3 has an oblong shape in plan view and includes a plurality of recessed parts 7 (wells) for containing cell-culture solution C, which serves as culture solution. The container main body 3 is a transparent member having a thin wall thickness and is made of, for example, a transparent plastic. The container main body 3 is one that is well known and may be, for example, a general well plate.

The presser-member-attached plate 5 has an oblong shape that corresponds to the container main body 3 and includes a plurality of presser members 9 corresponding to the recessed parts 7. The presser-member-attached plate 5 is a transparent member having a thin wall thickness and is made of, for example, a transparent plastic. The presser-member-attached plate 5 includes a plate-shaped main body 5a and a frame 5b, which is formed on an outer-perimetric surface of the main body 5a. The plurality of presser members 9 are provided on the main body 5a of the presser-member-attached plate 5. The presser members 9 are members that are removably fitted into upper sides of the recessed parts 7.

Figure 2:
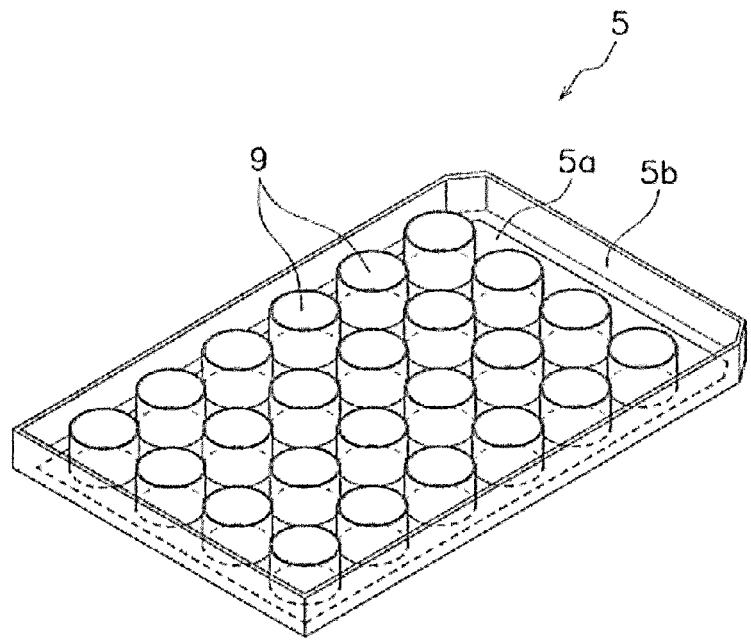
FIG. 2 is an oblique view of a presser-member-attached plate of the cell-culture container.
Figure 3:
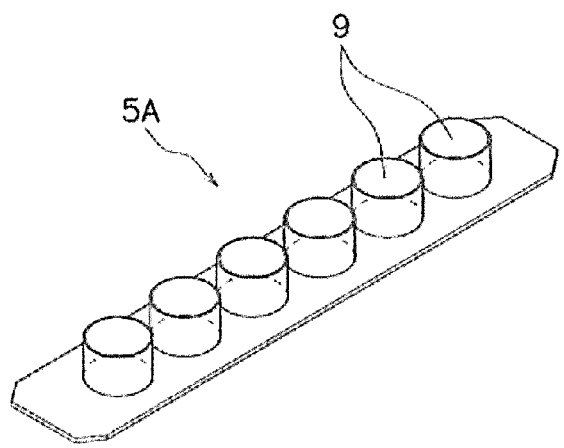
FIG. 3 is an oblique view of the presser-member-attached plate of the cell-culture container.

Furthermore, the presser-member-attached plate 5 shown in FIG. 2 includes 6×4, that is, a total of 24, of the presser members 9, and a presser-member-attached plate 5A shown in FIG. 3 includes 6×1, that is, a total of six, of the presser members 9. Four of the presser-member-attached plates 5A shown in FIG. 3 may be used for the container main body 3 shown in FIG. 1.

Figure 4:
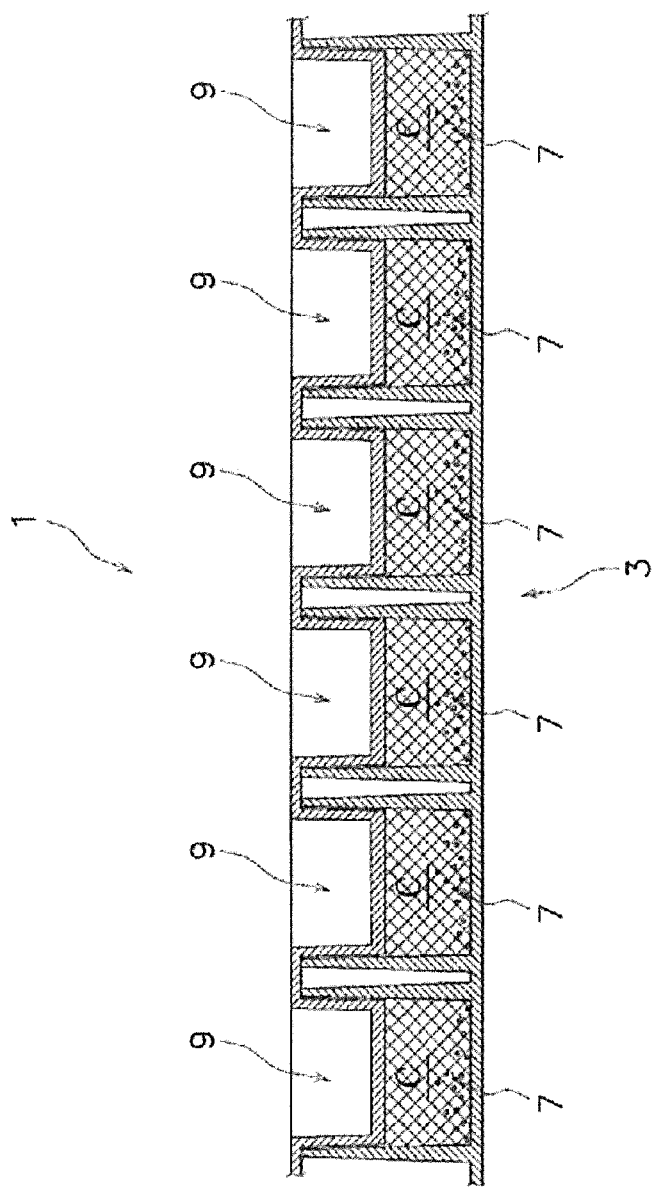
FIG. 4 is a cross-sectional view of the cell-culture container.

FIG. 4 is a cross-sectional view of the cell-culture container. As shown in FIG. 4, in the state wherein the presser-member-attached plate 5 is fitted to the container main body 3, the plurality of presser members 9 are inserted into the plurality of recessed parts 7, and thereby the recessed parts 7, which contain the cell-culture solution C, are sealed. Thereby, a decrease in the cell-culture solution C due to volatilization is prevented. The prevention of a reduction in the amount of the cell-culture solution C due to volatilization is important especially for recessed parts of small diameter.

Furthermore, although not shown, during cell culturing, the cell-culture container 1 is covered with a cover from above (that is, from above the presser-member-attached plate 5). The cover covers the container main body 3 and an upper part of the presser-member-attached plate 5. Thereby, contamination of the cell-culture solution is prevented.

The observation of cells in the cell-culture container 1 is performed by using various microscopes from below the recessed parts 7. Specifically, because the cells are often in a state in which they are adhered to bottom parts of the recessed parts 7, the cells are observed in that state. However, for a suspension culture, there are cases in which the cells suspended in the cell-culture solution C are observed.

(2) Detailed Structure

Figure 5:
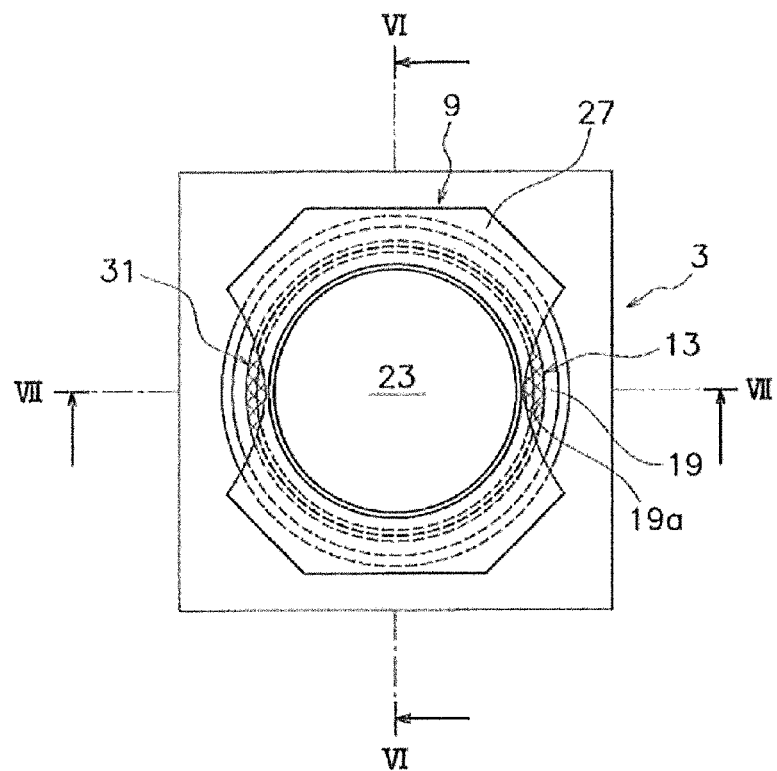
FIG. 5 is a partial plan view of the cell-culture container according to a first embodiment.
Figure 6:
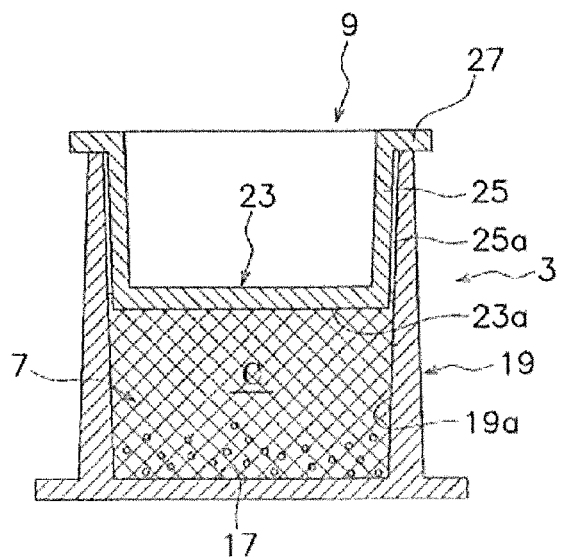
FIG. 6 is a cross-sectional view taken along line VI-VI in FIG. 5.
Figure 7:
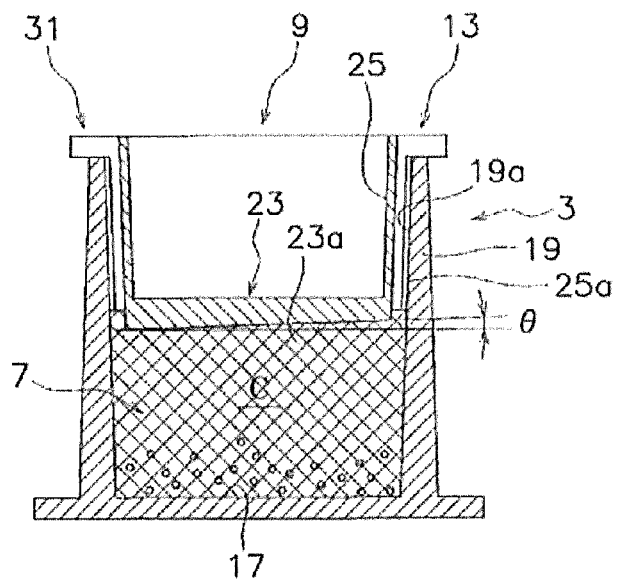
FIG. 7 is a cross-sectional view taken along line VII-VII in FIG. 5.

Next, the structures of the recessed parts 7 and the presser members 9 and the relationship of the two will be explained in detail, with reference to FIG. 5 to FIG. 7. FIG. 5 is a partial plan view of the cell-culture container. FIG. 6 is a cross-sectional view taken along line VI-VI in FIG. 5, and FIG. 7 is a cross-sectional view taken along line VII-VII in FIG. 5.

The presser member 9 has a lower surface 23a (discussed below) that makes contact with an upper surface of the cell-culture solution C in the seated state. Furthermore, the presser member 9 has a bubble-discharge part 13, which enables the discharge of bubbles in the cell-culture solution C to the exterior. In the present embodiment, the bubble-discharge part 13 is a recessed part that is formed on an outer circumferential surface of a tubular part 25 and provides communication between an outer-circumference side of the lower surface 23*a* (discussed below) and the exterior of the presser member 9.

The recessed part 7 includes a bottom part 17 and a tubular part 19. An inner circumferential surface 19*a* of the tubular part 19 extends substantially vertically in a longitudinal cross section.

The presser member 9 principally includes a lower-surface part 23 and the tubular part 25. The lower-surface part 23 is a circular flat plate in plan view. The tubular part 25 is fitted, with a slight gap, into the tubular part 19 of the recessed part 7. That is, an outer circumferential surface 25*a* of the tubular part 25 opposes the inner circumferential surface 19*a* of the tubular part 19 in a state wherein the outer circumferential surface 25*a* is proximate to the inner circumferential surface 19*a*. An outer circumferential edge of the lower-surface part 23 is connected to a lower end of the tubular part 25.

The presser member 9 further includes a flange part 27. In the present embodiment, for the sake of convenience of the explanation, the flange part 27 is explained as a member that is fixed to the main body 5*a* of the presser-member-attached plate 5, but the flange part 27 may be integrally formed with the main body 5*a*. The flange part 27 extends radially outward from the tubular part 25 and is seated on the upper surface of the tubular part 19 of the recessed part 7. Thus, because the presser member 9 is provided with the flange part 27, it is easy to remove the presser member 9 from the recessed part 7.

As shown in the figures, the bubble-discharge part 13 is formed in part of the presser member 9. The bubble-discharge part 13 is a structure that enables the discharge of bubbles inside the cell-culture solution C to the exterior. In the present embodiment, the bubble-discharge part 13 is a recessed part that is formed by notching part of the outer circumferential surface 25*a* of the tubular part 25 and, as shown in FIG. 7, this recessed part extends from the lower surface 23*a* of the lower-surface part 23 to the exterior of the cell-culture container 1. Furthermore, in the present embodiment, the flange part 27 is notched in an arcuate shape in plan view.

By thus providing the presser member 9 with the bubble-discharge part 13, the meniscus is eliminated by the presser member 9 and the retention of bubbles is also prevented. Accordingly, cells can be observed accurately and over a large surface area, that is, over a large area up to the outer circumferential edge of the recessed part 7.

The lower surface 23*a* of the lower-surface part 23 has a planar shape and, rather than being horizontal, is tilted (refer to angle 9 in FIG. 7). More specifically, the lower surface 23*a* is tilted such that it is highest in the vicinity of the bubble-discharge part 13. Thereby, bubbles in the vicinity of the lower surface 23*a* are guided toward the bubble-discharge part 13 along the lower surface 23*a*.

Furthermore, the tilt angle θ of the lower surface 23*a* is 1°-30° and more preferably is 1°-5°.

The lower surface 23*a* of the lower-surface part 23 is subject to a hydrophilization treatment. Accordingly, bubbles tend not to be retained in the vicinity of the lower surface 23*a*. A well-known technique (e.g., coating with a hydrophilic polymer) may be used as the hydrophilization treatment. In addition, the hydrophilization treatment prevents the cells cultured by the suspension culture from adhering to the lower surface 23*a* of the lower-surface part 23.

A liquid-supply part 31 is formed on the presser member 9. The liquid-supply part 31 is used to inject a liquid into the cell-culture solution C so as to cause the bubbles in the cell-culture solution C to move toward the bubble-discharge part 13. In the present embodiment, the liquid-supply part 31 is a recessed part that is formed by notching a part of the outer circumferential surface 25*a* of the tubular part 25, and this recessed part extends from the lower surface 23*a* of the lower-surface part 23 to the exterior of the cell-culture container 1.

In addition, the liquid-supply part 31 is formed at a position at which it opposes the bubble-discharge part 13 in the radial direction. That is, the liquid-supply part 31 is disposed at the lowest position of the lower surface 23*a*. When the liquid is injected via the liquid-supply part 31 into the cell-culture solution C, it causes the bubbles in the cell-culture solution C to move toward the bubble-discharge part 13. Accordingly, the bubbles tend not to be retained in the vicinity of the lower surface 23*a* of the presser member 9. For example, a pipette is used to supply the liquid.

Furthermore, the bubble-discharge part 13 and the liquid-supply part 31 enable insertion seeding via a pipette. Thereby, after the presser member 9 has been covered, the overall quantity and growth conditions of the cells can be adjusted.

As discussed above, the lower-surface part 23 of the presser member 9 makes contact with the upper surface of the cell-culture solution C, and thereby the meniscus problem is eliminated. Furthermore, the outer circumferential edge of the lower-surface part 23 extends to the vicinity of the inner circumferential surface 19*a* of the recessed part 7, and thereby the surface area of observation is increased.

Conventionally, in a recessed part having a diameter of, for example, approximately 7 mm, the area that can be observed without being affected by the meniscus has a diameter of approximately 1-3 mm; however, in the present embodiment, excluding the wall thickness of the presser member 9, an area with a diameter of approximately 5 mm becomes observable. Thereby, an area that was conventionally judged by conjecture becomes verifiable, and thus it becomes possible to accurately observe time-dependent changes and states.

The surface area of the opening portions of the presser member 9 created by slits is 1%-50%, and preferably 3%-30%, of the surface area of the lower-surface part 23. Thereby, a large surface area of observation can be ensured wherein problems do not arise in the observation of the cells, and it also is possible to remove the cell-culture solution C and the bubbles from below the lower-surface part 23.

Furthermore, the bubbles in the cell-culture solution C can be discharged to the exterior of the cell-culture container 1 via the bubble-discharge part 13. In addition, the discharge of the bubbles can be performed reliably and rapidly owing to the tilt and the hydrophilization treatment of the lower surface 23*a* and, furthermore, via the liquid-supply part 31.

An operation of fitting the presser member 9 into the recessed part 7 will be explained simply. First, the cell-culture solution C is injected into the recessed part 7. The amount of the cell-culture solution C at this time is, for example, to reach the position at which the lower surface 23*a* of the presser member 9 makes contact with the upper surface of the cell-culture solution. Next, the presser member 9 is fitted into the recessed part 7. This results in a state wherein, as shown in FIG. 7 for example, the liquid surface of the cell-culture solution C is pressed against the lower surface 23a. Furthermore, a portion of the cell-culture solution C enters the bubble-discharge part 13 and the liquid-supply part 31.

Furthermore, the tilt of the lower surface 23a may be omitted or may have some other shape. For example, the lower surface 23a may be a two-step tilted surface wherein a tilt angle in the vicinity of the bubble-discharge part is large. In addition, the hydrophilization treatment of the lower surface 23a may be omitted or may be performed partially. Furthermore, the liquid-supply part 31 may be omitted or may have some other shape.

Concrete examples of the dimensions of the presser member and the recessed part according to the abovementioned embodiment will now be explained. Furthermore, in the concrete examples below, illustrative examples are given of sizes of wells in which a meniscus is conspicuous, but the present invention is not limited to these numeric values. Generally, types of container main bodies include those with 6, 12, 24, 48, 96, and 384 wells. In the case of 24 wells, the inner diameter of each presser member is 8.0-14.0 mm, the longitudinal length of each presser member (excluding the flange) is 3.0-10.0 mm, the outer diameter of each presser member is 8.0-14.0 mm, and the inner diameter of the bottom surface of each recessed part is 14.0-17.0 mm. In the case of 96 wells, the inner diameter of each presser member is 4.0-5.0 mm, the longitudinal length of each presser member (excluding the flange) is 3.0-10.0 mm, the outer diameter of each presser member is 4.0-5.0 mm, and the inner diameter of the bottom surface of each recessed part is 5.0-7.0 mm.

2. Second Embodiment

Figure 8:
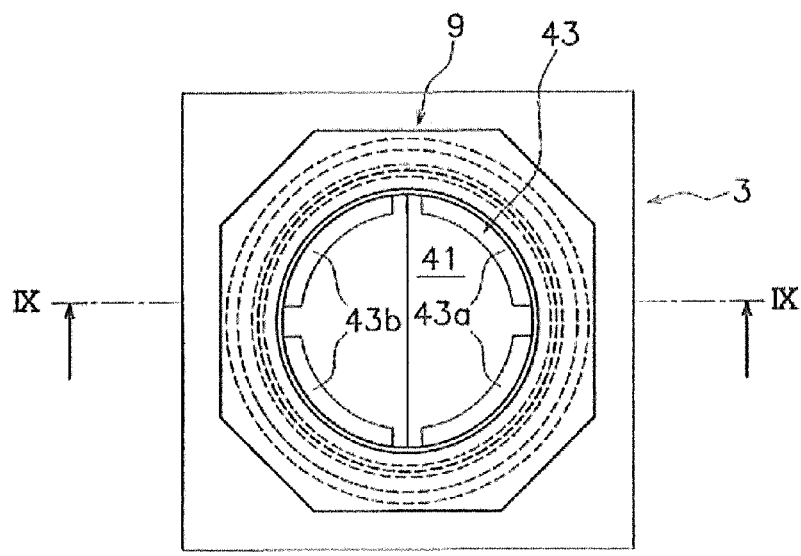
FIG. 8 is a partial plan view of the cell-culture container according to a second embodiment.
Figure 9:
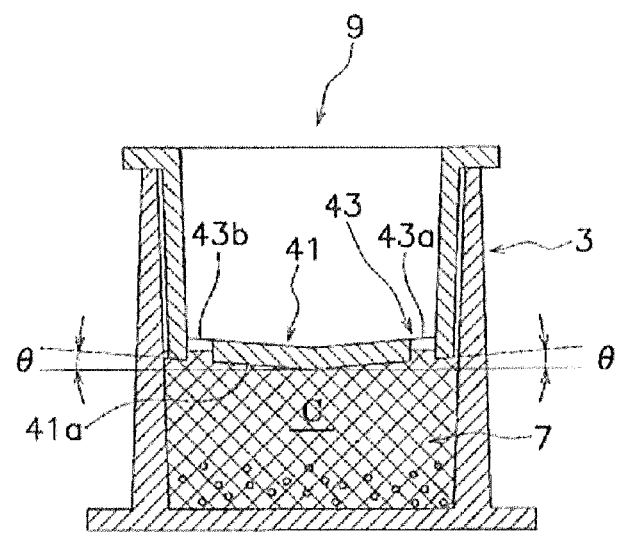
FIG. 9 is a cross-sectional view taken along line IX-IX in FIG. 8.

A second embodiment is explained below, with reference to FIG. 8 and FIG. 9. FIG. 8 is a partial plan view of the cell-culture container. FIG. 9 is a cross-sectional view taken along line IX-IX in FIG. 8.

Furthermore, the basic configuration of the presser member and the recessed part is the same as in the embodiment described above. The explanation below focuses on points of difference.

The presser member 9 has a lower surface 41a (discussed below) that makes contact with the upper surface of the cell-culture solution C in the fitted state. Furthermore, the presser member 9 has a bubble-discharge part 43 that enables the discharge of bubbles in the cell-culture solution C to the exterior. In the present embodiment, the bubble-discharge part 43 is a plurality of grooves that is formed on an outer circumferential edge of a lower-surface part 41, extends arcuately, and passes through the lower-surface part 41 in the up-down direction. Specifically, the bubble-discharge part 43 has a pair of first grooves 43a on the right side of the figure and a pair of second grooves 43b on the left side of the figure. The pair of first grooves 43a on the right side in the figure extends over the entire right-side half of the outer circumferential edge of the lower-surface part 41. In addition, the pair of second grooves 43b on the left side in the figure extends entirely over the left-side half of the outer circumferential edge of the lower-surface part 41.

By thus providing the presser member 9 with the bubble-discharge part 43 in this manner, the presser member 9 eliminates the meniscus and also prevents retention of bubbles. Accordingly, the cells can be observed accurately and over a large surface area, that is, the large area extending to the outer circumferential edge of the recessed part 7.

The lower surface 41a of the lower-surface part 41 is divided in two portions on the left and right of the figure, the portions having tilted planar shapes that tilt from the left-right center of the figure toward the left and right sides in the figure (refer to angle θ in FIG. 9). More specifically, the right side portion of the lower surface 41a is tilted such that the vicinity of the midway point between the pair of first grooves 43a is highest. The left side portion of the lower surface 41a is tilted such that the vicinity of the midway point between the pair of second grooves 43b is highest. Thereby, bubbles in the vicinity of the lower surface 41a are guided toward the pair of first grooves 43a and the pair of second grooves 43b along the lower surface 41a.

An operation of fitting the presser member 9 into the recessed part 7 will be explained simply. First, the cell-culture solution C is injected into the recessed part 7. The amount of the cell-culture solution C at this time is, for example, a position at which the lower surface 41a of the presser member 9 makes contact with the upper surface of the cell-culture solution C. Next, the presser member 9 is fitted into the recessed part 7. Thereupon, as shown in FIG. 9 for example, a state results wherein the liquid surface of the cell-culture solution C is pressed against the lower surface 41a. In this case, a portion of the cell-culture solution C enters the first grooves 43a and the second grooves 43b of the bubble-discharge part 43. Furthermore, in FIG. 9, the liquid surface of the cell-culture solution is located within the first grooves 43a and the second grooves 43b, but a portion of the cell-culture solution C may go beyond the first grooves 43a and the second grooves 43b and spill over to the upper side of the lower-surface part 41.

The effects obtained by the present embodiment are the same as those obtained by the first embodiment. In addition, the number, positions, and shape of the grooves that serve as the bubble-discharge part can be modified as needed.

In addition, the bubble-discharge part formed in the lower-surface part may have a hole shape instead of a groove shape.

The shape of the lower surface 23a is not limited to that in the abovementioned embodiment. The lower surface may be a flat surface, the entirety of which extends horizontally, or may be a plurality of tilted planar surfaces that is formed such that it corresponds to the grooves.

3. Third Embodiment

Figure 10:
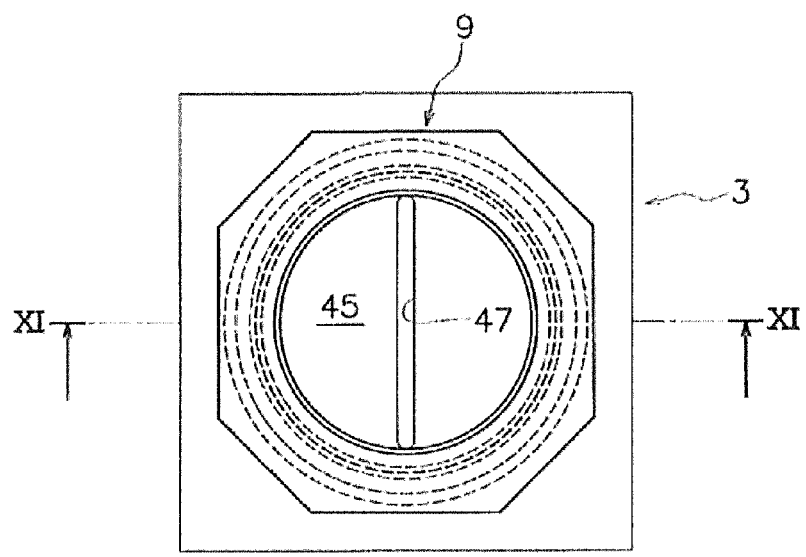
FIG. 10 is a partial plan view of the cell-culture container according to a third embodiment.
Figure 11:
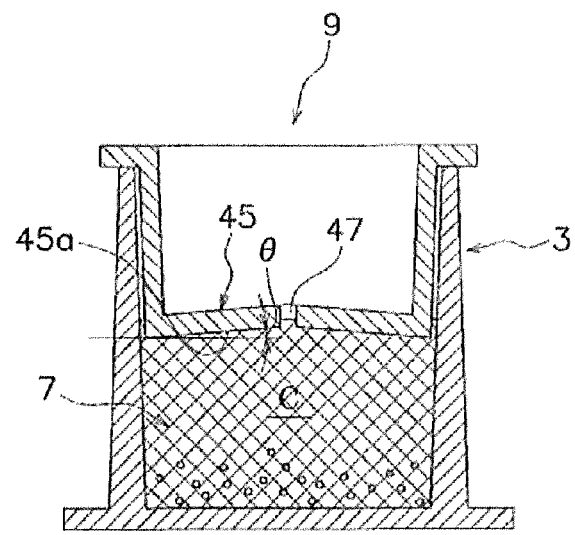
FIG. 11 is a cross-sectional view taken along line XI-XI in FIG. 10.

A third embodiment is explained below, with reference to FIG. 10 and FIG. 11. FIG. 10 is a partial plan view of the cell-culture container. FIG. 11 is cross-sectional view taken along line XI-XI in FIG. 10.

Furthermore, the basic configuration of the presser member and the recessed part is the same as in the embodiments described above. The explanation below focuses on points of difference.

The presser member 9 has a lower surface 45a (discussed below) that makes contact with the upper surface of the cell-culture solution C in the fitted state. Furthermore, the presser member 9 has a bubble-discharge part 47 that enables the discharge of bubbles in the cell-culture solution C to the exterior. In the present embodiment, the bubble-discharge part 47 is a groove that is formed in the left-right center of the lower-surface part 41 and extends in a straight line. Specifically, in the figure, the bubble-discharge part 47 extends from the outer circumferential edge to the outer circumferential edge of the lower-surface part 41.

By providing the presser member 9 with the bubble-discharge part 47 in this manner, the presser member 9 eliminates the meniscus and also prevents retention of bubbles. Accordingly, the cells can be observed accurately and over a large surface area, that is, the large area extending to the outer circumferential edge of the recessed part 7.

The lower surface 45a of a lower-surface part 45 is divided into two portions on the left and right of the figure, the portions having tilted planar shapes that tilt from the left-right center of the figure toward the left and right sides in the figure (refer to angle θ in FIG. 11). More specifically, the right-side portion of the lower surface 45a in the figure is tilted such that the vicinity of the bubble-discharge part 47 is highest. The left-side portion of the lower surface 45a in the figure is tilted such that the vicinity of the bubble-discharge part 47 is highest. Thereby, bubbles in the vicinity of the lower surface 45a are guided toward the bubble-discharge part 47 along the lower surface 45a.

The effects obtained by the present embodiment are the same as those obtained by the first through second embodiments.

In addition, the number, positions, and shape of the grooves that serve as the bubble-discharge part can be modified as needed. In addition, the bubble-discharge part formed in the lower-surface part may have a hole shape instead of a groove shape.

The shape of the lower surface 45a is not limited to that in the abovementioned embodiment. The lower surface may be a flat surface, the entirety of which extends horizontally.

4. Fourth Embodiment

Figure 12:
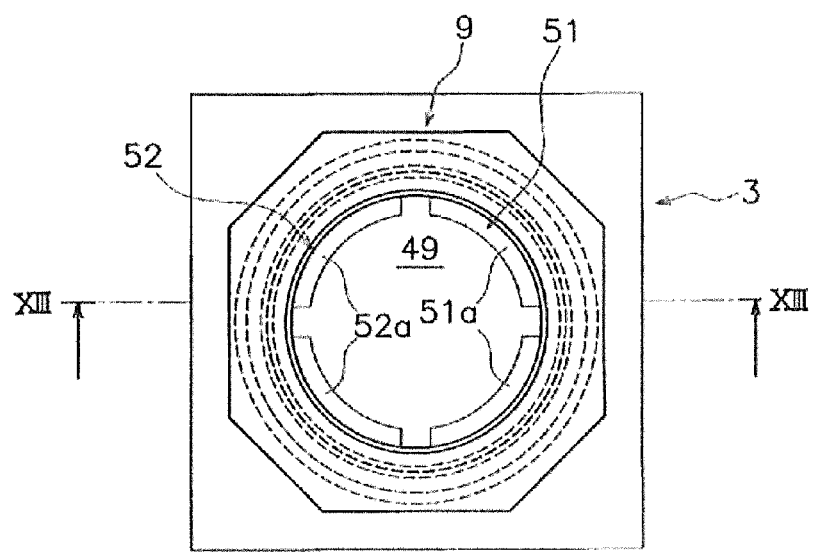
FIG. 12 is a partial plan view of the cell-culture container according to a fourth embodiment.
Figure 13:
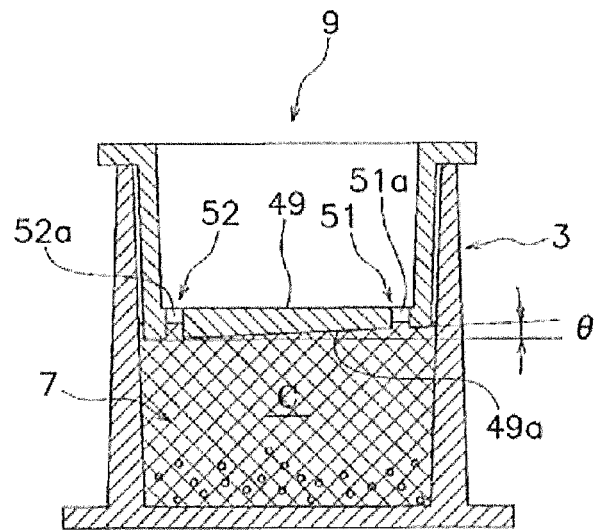
FIG. 13 is a cross-sectional view taken along line XIII-XIII in FIG. 12.

A fourth embodiment is explained below, with reference to FIG. 12 and FIG. 13. FIG. 12 is a partial plan view of the cell-culture container. FIG. 13 is a cross-sectional view taken along line XIII-XIII in FIG. 12.

Furthermore, the basic configuration of the presser member and the recessed part is the same as in the embodiments described above. The explanation below focuses on points of difference.

The presser member 9 has a lower surface 49a (discussed below) that makes contact with the upper surface of the cell-culture solution C in the fitted state. Furthermore, the presser member 9 has a bubble-discharge part 51 that enables the discharge of bubbles in the cell-culture solution C to the exterior. In the present embodiment, the bubble-discharge part 51 is grooves that are formed on an outer circumferential edge of a lower-surface part 49 and extend arcuately. Specifically, the bubble-discharge part 51 has a pair of first grooves 51a on the right side in the figure. The pair of first grooves 51a extends over the entire right-side half of the outer circumferential edge of the lower-surface part 49 in the figure.

By providing the presser member 9 with the bubble-discharge part 51 in this manner, the retention of bubbles is also prevented. Accordingly, cells can be observed accurately and over a large surface area, that is, the large area extending to the outer circumferential edge of the recessed part 7.

The lower surface 49a of the lower-surface part 49 has a planar shape but is tilted instead of being horizontal (refer to angle θ in FIG. 13). More specifically, the lower surface 49a is tilted such that the vicinity midway between the pair of first grooves 51a of the bubble-discharge part 51 is highest. Thereby, bubbles in the vicinity of the lower surface 49a are guided toward the bubble-discharge part 51 along the lower surface 49a.

A liquid-supply part 52 is formed on the presser member 9. The liquid-supply part 52 is used to inject the liquid into the cell-culture solution C so as to cause the bubbles in the cell-culture solution C to move toward the bubble-discharge part 51. In the present embodiment, the liquid-supply part 52 is grooves that are formed in the outer circumferential edge of the lower-surface part 49 and extend arcuately. Specifically, the liquid-supply part 52 has a pair of second grooves 52a on the left side of the figure. The pair of second grooves 52a extends over the entire left-side half of the outer circumferential edge of the lower-surface part 49 in the figure.

In addition, the liquid-supply part 52 is formed at a position at which it opposes the bubble-discharge part 51 in the radial direction. That is, the midway point between the pair of second grooves 52a of the liquid-supply part 52 is the lowest position of the lower surface 49a. When the liquid is injected via the liquid-supply part 52 into the cell-culture solution C, it is causes the bubbles in the cell-culture solution C to move toward the bubble-discharge part 51. Accordingly, the bubbles tend not to be retained in the vicinity of the lower surface 49a of the presser member 9. For example, a pipette is used to supply the liquid.

The effects obtained by the present embodiment are the same as those obtained by the first through third embodiments.

Furthermore, the tilt of the lower surface 49a may be omitted or have some other shape. In addition, the hydrophilization treatment of the lower surface 49a may be omitted or may be performed partially. Furthermore, the liquid-supply part 52 may be omitted or may have some other shape.

5. Fifth Embodiment

Figure 14:
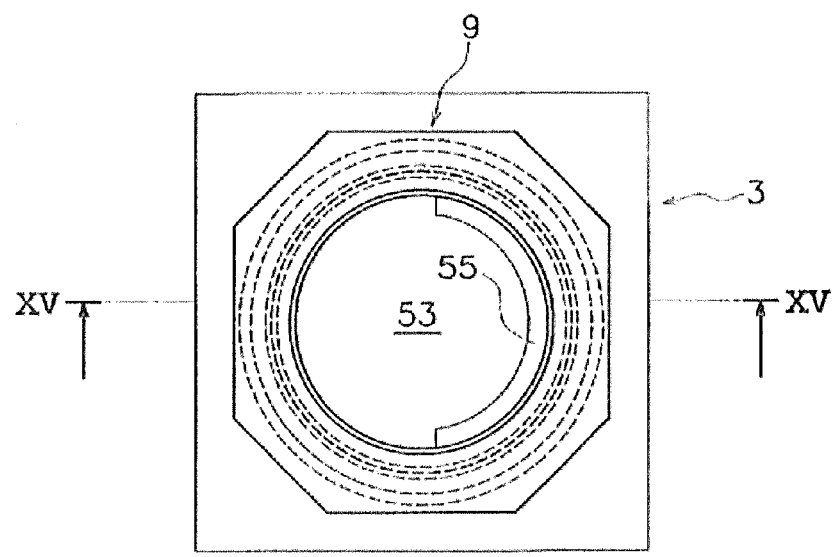
FIG. 14 is a partial plan view of the cell-culture container according to a fifth embodiment.
Figure 15:
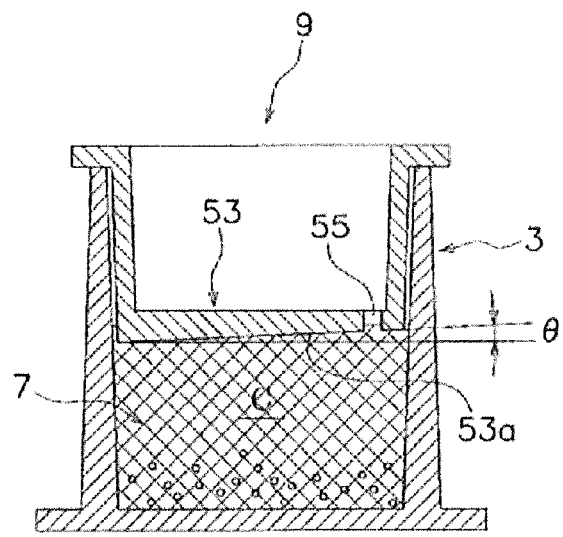
FIG. 15 is a cross-sectional view taken along line XV-XV in FIG. 14.

A fifth embodiment is explained below, with reference to FIG. 14 and FIG. 15. FIG. 14 is a partial plan view of the cell-culture container. FIG. 15 is a cross-sectional view taken along line XV-XV in FIG. 14.

Furthermore, the basic configuration of the presser member and the recessed part is the same as in the embodiments described above. The explanation below focuses on points of difference.

The presser member 9 has a lower surface 53a (discussed below) that makes contact with the upper surface of the cell-culture solution C in the fitted state. Furthermore, the presser member 9 has a bubble-discharge part 55 that enables the discharge of bubbles in the cell-culture solution C to the exterior. In the present embodiment, the bubble-discharge part 55 is a groove that is formed on an outer circumferential edge of a lower-surface part 53 and extends arcuately. Specifically, the bubble-discharge part 55 is a groove that extends along the right-side half of the outer circumferential edge of the lower-surface part 53 in the figure.

By providing the presser member 9 with the bubble-discharge part 55 in this manner, the presser member 9 eliminates the meniscus and also prevents retention of bubbles. Accordingly, cells can be observed accurately and over a large surface area, that is, the large area extending to the outer circumferential edge of the recessed part 7.

The lower surface 53a of the lower-surface part 53 has a planar shape but is tilted (refer to angle θ in FIG. 15) instead of horizontal. More specifically, the lower surface 53a is tilted such that the vicinity of the midway part of the bubble-discharge part 55 is highest.

Thereby, bubbles in the vicinity of the lower surface 53a are guided toward the bubble-discharge part 55 along the lower surface 53a.

The effects obtained by the present embodiment are the same as those obtained by the first through fourth embodiments.

The number, positions, and shape of the grooves that serve as the bubble-discharge part can be modified as needed. The bubble-discharge part formed in the lower-surface part may have a hole shape instead of a groove shape.

The shape of the lower surface of the lower-surface part is not limited to the present embodiment. The lower surface may be a flat surface, the entirety of which extends horizontally.

6. Sixth Embodiment

Figure 16:
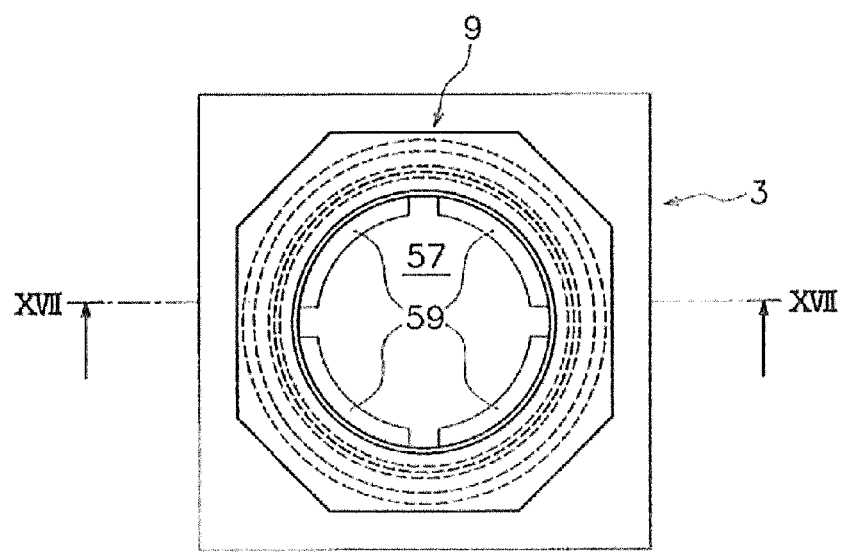
FIG. 16 is a partial plan view of the cell-culture container according to a sixth embodiment.
Figure 17:
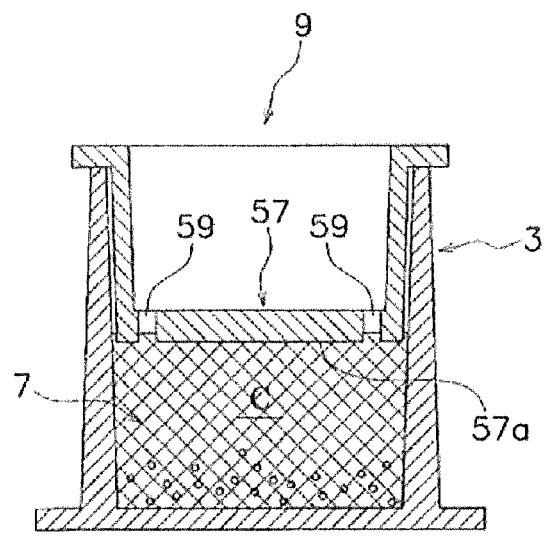
FIG. 17 is a cross-sectional view taken along line XVII-XVII in FIG. 16.

A sixth embodiment is explained below, with reference to FIG. 16 and FIG. 17. FIG. 16 is a partial plan view of the cell-culture container. FIG. 17 is a cross-sectional view taken along line XVII-XVII in FIG. 16.

Furthermore, the basic configuration of the presser member and the recessed part is the same as in the embodiments described above. The explanation below focuses on points of difference.

The presser member 9 has a lower surface 57a (discussed below) that makes contact with the upper surface of the cell-culture solution C in the fitted state. Furthermore, the presser member 9 has a bubble-discharge part 59 that enables the discharge of bubbles in the cell-culture solution C to the exterior. In the present embodiment, the bubble-discharge part 59 is a plurality of grooves that is formed on an outer circumferential edge of a lower-surface part 57 and extends arcuately. Specifically, a total of four grooves are formed.

By providing the presser member 9 with the bubble-discharge part 59 in this manner, the presser member 9 eliminates the meniscus and also prevents the retention of bubbles. Accordingly, cells can be observed accurately and over a large surface area, that is, the large area extending to the outer circumferential edge of the recessed part 7.

The lower surface 57a of the lower-surface part 57 is a planar end surface that extends horizontally.

Furthermore, in the present embodiment, any bubble-discharge part 59 of the plurality of bubble-discharge parts 59 can be used as the liquid-supply part.

The effects obtained by the present embodiment are the same as those obtained by the first through fifth embodiments. In addition, the number, positions, and shape of the grooves, which are the bubble-discharge parts, can be modified as needed.

In addition, the bubble-discharge part formed in the lower-surface part may have a hole shape instead of a groove shape.

7. Seventh Embodiment

Figure 18:
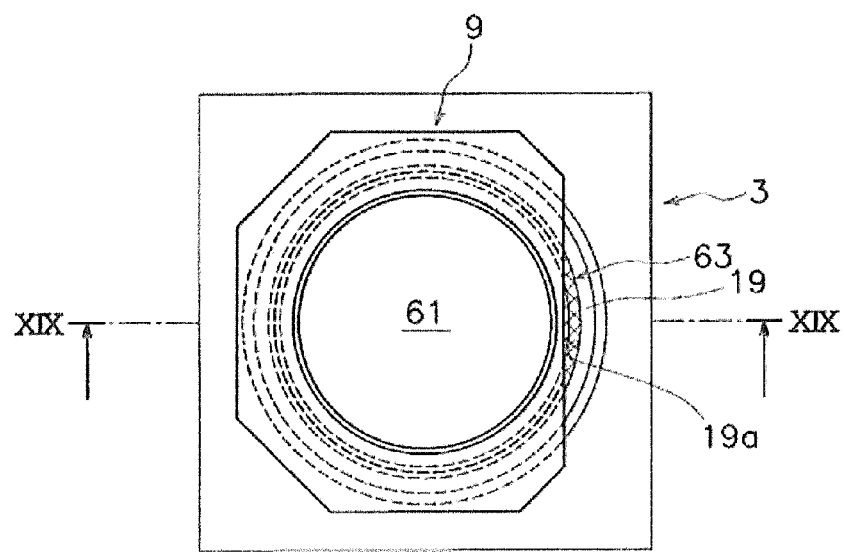
FIG. 18 is a partial plan view of the cell-culture container according to a seventh embodiment.
Figure 19:
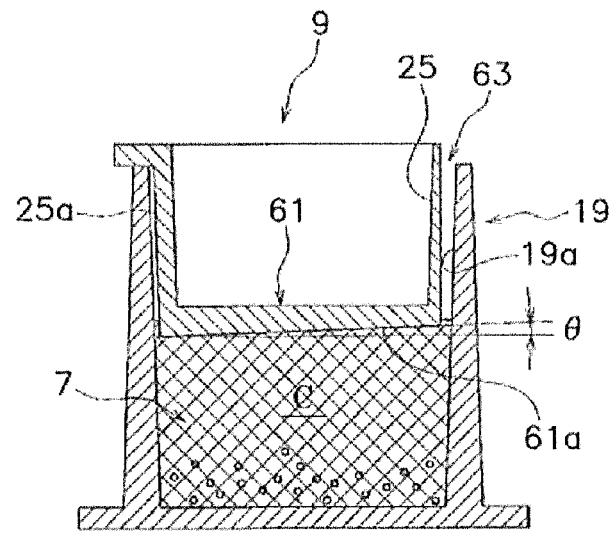
FIG. 19 is a cross-sectional view taken along line XIX-XIX in FIG. 18.

Next, a seventh embodiment is explained below, with reference to FIG. 18 and FIG. 19. FIG. 18 is a partial plan view of the cell-culture container. FIG. 19 is a cross-sectional view taken along line XIX-XIX in FIG. 18.

Furthermore, the basic configuration of the presser member and the recessed part is the same as in the embodiments described above. The explanation below focuses on points of difference.

The presser member 9 has a lower surface 61a (discussed below) that makes contact with the upper surface of the cell-culture solution C in the fitted state. Furthermore, the presser member 9 has a bubble-discharge part 63 that enables the discharge of bubbles in the cell-culture solution C to the exterior.

In the present embodiment, the bubble-discharge part 63 is a recessed part that is formed by notching part of the outer circumferential surface 25a of the tubular part 25, and this recessed part extends from the lower surface 61a of a lower-surface part 61 to the exterior of the cell-culture container 1. Furthermore, in the present embodiment, the flange part 27 is notched in a straight line in plan view.

By thus providing the presser member 9 with the bubble-discharge part 63 in this manner, the presser member 9 eliminates the meniscus and also prevents retention of bubbles. Accordingly, the cells can be observed accurately and over a large surface area, that is, the large area extending to the outer circumferential edge of the recessed part 7.

The lower surface 61a of the lower-surface part 61 has a planar shape but is tilted (refer to angle θ in FIG. 19) instead of horizontal. More specifically, the lower surface 61a is tilted such that the vicinity of the bubble-discharge part 63 is highest. Thereby, bubbles in the vicinity of the lower surface 61a are guided toward the bubble-discharge part 63 along the lower surface 61a.

The effects obtained by the present embodiment are the same as those obtained by the first through sixth embodiments.

8. Eighth Embodiment

In the first through seventh embodiments, the lower-surface parts 23, 53, 63 are disposed at positions comparatively spaced apart from the bottom part 17, but the present invention is not particularly limited to these positions.

Figure 20:
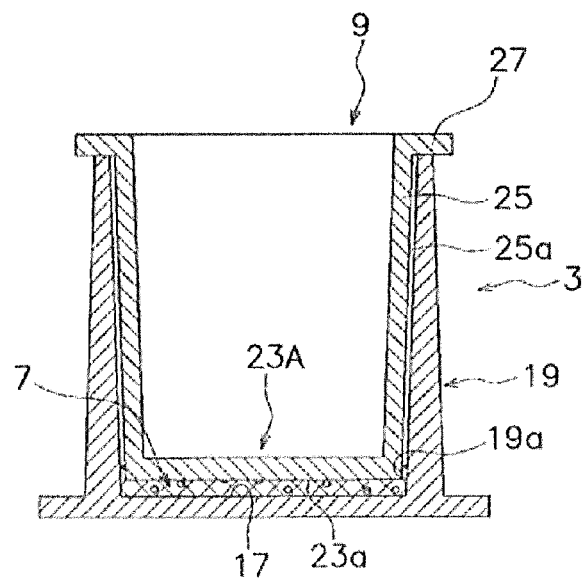
FIG. 20 is a cross-sectional view of the cell-culture container according to an eighth embodiment.

A ninth embodiment will now be explained, with reference to FIG. 20. FIG. 20 is a cross-sectional view of the cell-culture container.

Furthermore, the basic configuration of the presser member and the recessed part is the same as in the embodiments described above. The explanation below focuses on points of difference.

As is clear from the figure, a lower-surface part 23A is disposed proximate to the bottom part 17. This structure can also be adapted to any of the first through eighth embodiments and obtains effects the same as those in those embodiments.

9. Ninth Embodiment

In the first through eighth embodiments, the present invention is adapted to containers for observing cells in a culture solution, but the present invention can also be adapted to other types of containers.

A cell-culture container for forming spheroids will now be explained, with reference to FIG. 21 to FIG. 24. FIG. 21 to FIG. 24 are cross-sectional views of the cell-culture container. FIG. 25 is a top view of the presser member.

Furthermore, the basic configuration of the presser member and the recessed part are the same as in the embodiments described above. The explanation below focuses on points of difference.

Figure 21:
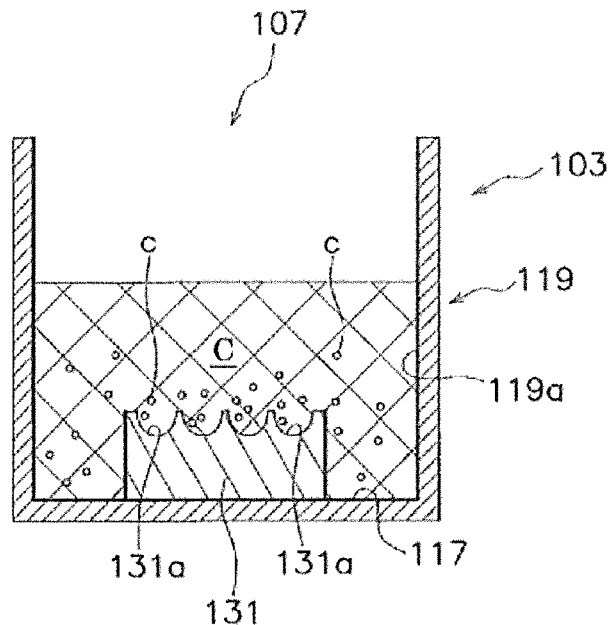
FIG. 21 is a cross-sectional view of the cell-culture container according to a ninth embodiment.

FIG. 21 shows a container main body 103 of the cell-culture container. The container main body 103 is a container, the upper side of which is open, which holds the cell-culture solution C. The cell-culture solution C contains a large number of the seed cells c.

A microwell member 131 is installed on a bottom part 117 of a recessed part 107. The microwell member 131 is a member having a plurality of microwells 131a. Specifically, the microwell member 131 has the numerous microwells 131a on its upper surface (corresponding to a first portion). The diameter of each microwell 131a is, for example, 30-1,500 µm and preferably is 50-300 µm. The depth of each microwell 131a is, for example, 30-1,500 µm and preferably is 50-300 µm.

In the present embodiment, the microwell member 131 is provided at the center of the bottom part 117, and the upper surface of the microwell member 131 is disposed relatively spaced apart and upward from the bottom part 117. Consequently, in the bottom part 117, the outer-circumference side of the microwell member 131 is a surface (corresponding to a second portion) that is lower than the upper surface of the microwell member 131.

Figure 22:
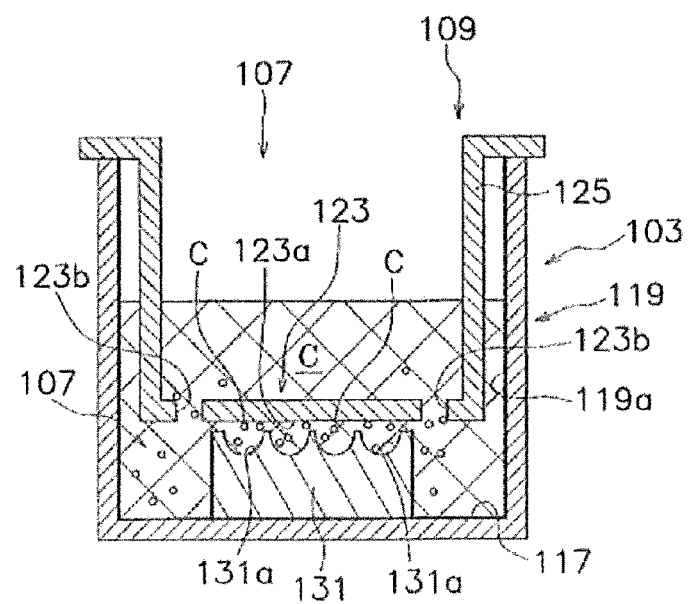
FIG. 22 is a cross-sectional view of the cell-culture container.

As shown in FIG. 22, a presser member 109 is inserted into the recessed part 107 of the container main body 103. As shown in FIG. 22 and FIG. 25, the presser member 109 has a discoidal lower-surface part 123. A lower surface 123a of the lower-surface part 123 is disposed proximate to the upper surface of the microwell member 131 (the portion at which the microwells 131a are formed). The dimension between the lower surface 123a of the lower-surface part 123 and the upper surface of the microwell member 131 should be shorter than the diameter of a spheroid S, for example, 0-300 µm. In addition, in the lower-surface part 123, a plurality of bubble-discharge parts 123b is formed in a portion radially outward of the microwell member 131. That is, the bubble-discharge parts 123b are provided such that they correspond to the second portion of the bottom part 117 (the portion at which there are no microwells 131a). The bubble-discharge parts 123b are dotlike through holes. Accordingly, bubbles in the space below the lower-surface part 123 (e.g., the plurality of microwells 131a and the periphery of the microwell member 131) are easily discharged to the exterior.

First, the seed cells c are seeded. Specifically, as shown in FIG. 21, the cell-culture solution C is injected into the recessed part 107. The cell-culture solution C is a suspension including a liquid culture medium and the seed cells c, which are evenly dispersed in the culture medium. The seed cells c are adherent, for example: cancer cells, such as human osteosarcoma cells; hepatocytes; and the like. A well-known culture medium suited to the culturing of adherent cells is used as the culture medium. In the case above, the seed cells c are implanted by being dropped as far as the microwells 131a.

Subsequently, as shown in FIG. 22, the presser member 109 is fitted into the recessed part 107.

Figure 23:
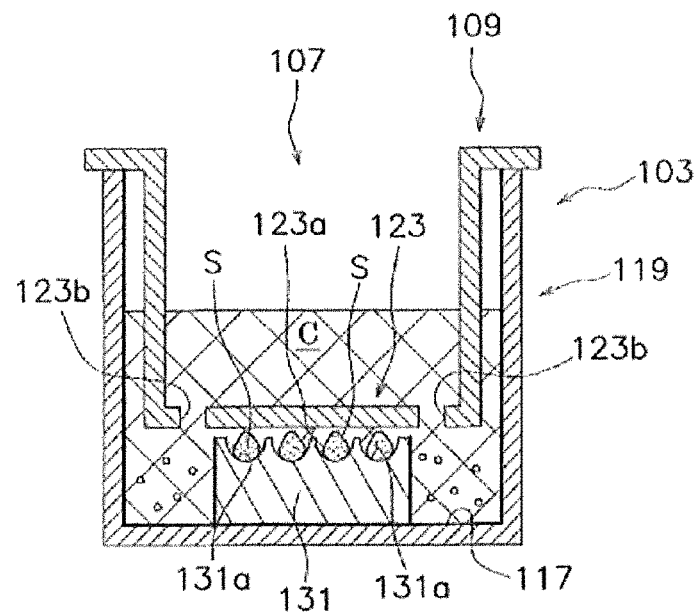
FIG. 23 is a cross-sectional view of the cell-culture container.

Furthermore, as shown in FIG. 23, the spheroids S are formed by the agglomeration of the plurality of seed cells c inside each microwell 131a. In the present cell-culture container, the lower-surface part 123 is disposed above the plurality of microwells 131a inside the recessed part 107, and the movement of each spheroid S that has grown inside its corresponding microwell 131a is limited such that each spheroid S does not separate from the corresponding microwell 131a. Accordingly, the spheroids S are formed stably in the cell-culture container.

An apparatus that supplies and discharges the culture medium to and from the interior of the recessed part 107 may be provided using a pipe and a pump, which are not shown. Thereby, new culture medium can be injected into the recessed part 107 through an inflow port, and culture medium inside the cell-culture container can be discharged through an outflow port. That is, when the seed cells c are being formed into the spheroids S in the microwells 131a, the culture medium inside the recessed part 107 is replaced.

In the abovementioned replacement of the culture medium, a flow arises in the culture medium inside the recessed part 107; however, at this time, the spheroids S do not flow out of the microwells 131a because the lower-surface part 123 is pressed against the spheroids S. Accordingly, the outflow of the spheroids S is prevented.

Owing to the culture medium replacement discussed above, the circulation of the culture medium supplies nutrients and oxygen to the cells even while being cultured, and therefore the cells grow healthfully. As a result, large spheroids S that require a relatively long culture time can be formed; furthermore, the formed spheroids S can be preserved for a long time. In addition, owing to the culture medium replacement, cell waste and waste matter that did not form into spheroids S are removed.

Figure 24:
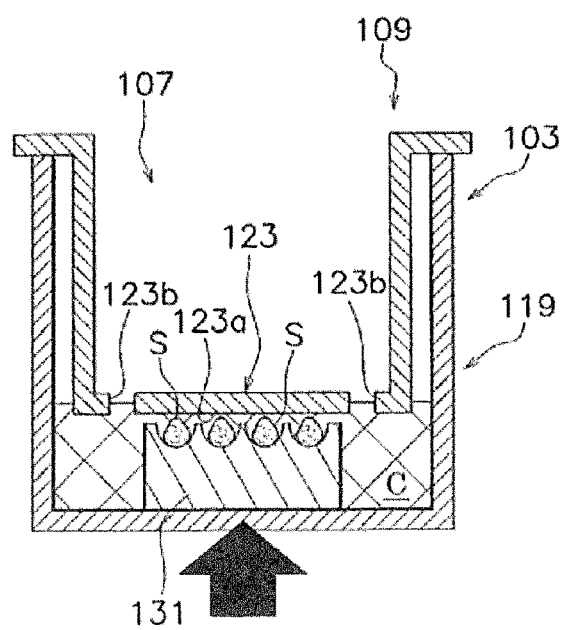
FIG. 24 is a cross-sectional view of the cell-culture container.
Figure 25:
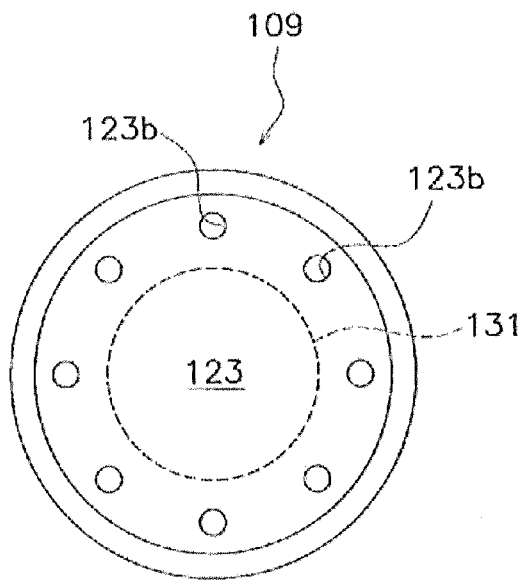
FIG. 25 is a top view of a presser member.

As shown in FIG. 24, after the amount of the cell-culture solution C has decreased and the cell-culture solution C no longer exists on the upper side of the lower-surface part 123, the spheroids S are observed from below the container main body 103. At this time, the lower surface 123a of the lower-surface part 123 makes contact with the upper surface of the cell-culture solution C, and therefore the meniscus is eliminated. As a result, the spheroids S that have grown in the plurality of microwells 131a in the container main body 103 can be observed accurately.

In addition, because the bubble-discharge parts are not formed at positions corresponding to the plurality of microwells 131a in the lower-surface part 123, the spheroids S that have grown in the plurality of microwells 131a can be observed accurately.

10. Tenth Embodiment

In the ninth embodiment, the bubble-discharge parts are a plurality of holes, but the shape of the bubble-discharge parts is not limited thereto.

Figure 26:
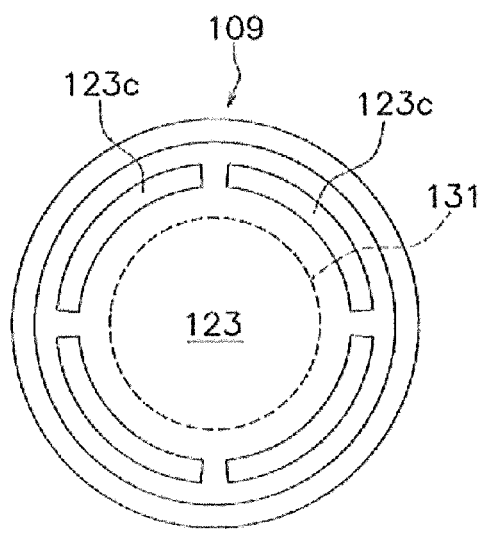
FIG. 26 is a top view of the presser member according to a tenth embodiment.

Another embodiment of the presser member will be explained, with reference to FIG. 26. FIG. 26 is a top view of the presser member. Furthermore, the basic configuration of the presser member and the recessed part is the same as in the embodiments discussed above. The explanation below focuses on points of difference.

In the lower-surface part 123, a plurality of bubble-discharge parts 123c is formed in a portion radially outward of the microwell member 131. The bubble-discharge parts 123c are arcuate through grooves extending in the circumferential direction.

The shape, number, and positions of the through holes formed in the lower-surface part and serving as the bubble-discharge parts are not particularly limited. In addition, the bubble-discharge parts are not limited to being through holes formed in the lower-surface part. The bubble-discharge parts may be notches, slits, or through holes formed between a tubular part 125 of the presser member 109 and a tubular part 119 of the container main body 103. The bubble-discharge parts are not formed at positions corresponding to the plurality of microwells 131a in the lower-surface part 123 (that is, at the center part and the midway part in the radial direction), and therefore the spheroids S grown in the plurality of microwells 131a can be accurately observed.

11. Eleventh Embodiment

In the ninth embodiment, the lower-surface part of the presser member has a flat shape, but the shape of the lower-surface part is not particularly limited.

Figure 27:
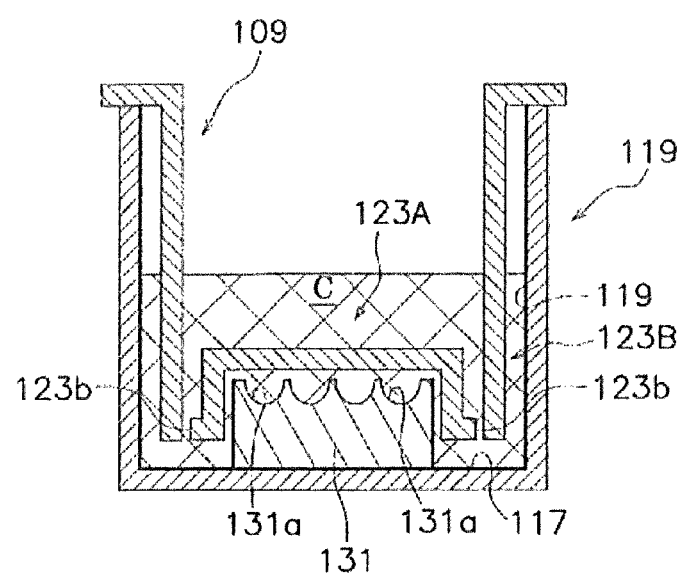
FIG. 27 is a cross-sectional view of the cell-culture container according to an eleventh embodiment.

Another embodiment of the presser member 109 will now be explained, with reference to FIG. 27. FIG. 27 is a cross-sectional view of the cell-culture container. Furthermore, the basic configuration of the presser member and the recessed part is the same as in the embodiments described above. The explanation below focuses on points of difference.

As shown in the figure, the lower-surface part of the presser member 109 includes a flat presser part 123A and a ring-shaped protruding part 123B. The presser part 123A is disposed proximate to the upper surface of the microwell member 131. The ring-shaped protruding part 123B is formed on the outer circumferential edge of the presser part 123A and extends downward. That is, the protruding part 123B is disposed so as to surround the outer-circumference side of the microwell member 131. The plurality of bubble-discharge parts 123b is formed on the bottom surface of the protruding part 123B. The shapes of the bubble-discharge parts 123b are dotlike through holes, arcuate through holes, or a combination thereof.

The bubble-discharge parts are not formed at positions corresponding to the plurality of microwells 131a in the lower-surface part (that is, at the presser part 123A), and therefore the spheroids S grown in the plurality of microwells 131a can be accurately observed.

12. Twelfth Embodiment

Particularly in the eighth through eleventh embodiments, it is required to accurately control the dimension between the lower-surface part of the presser member and the members therebelow. However, because the presser member is used by being pressed onto the culture medium in the culture container, there is conceivably a problem in that the presser member will adversely float owing to its buoyancy.

Figure 28:
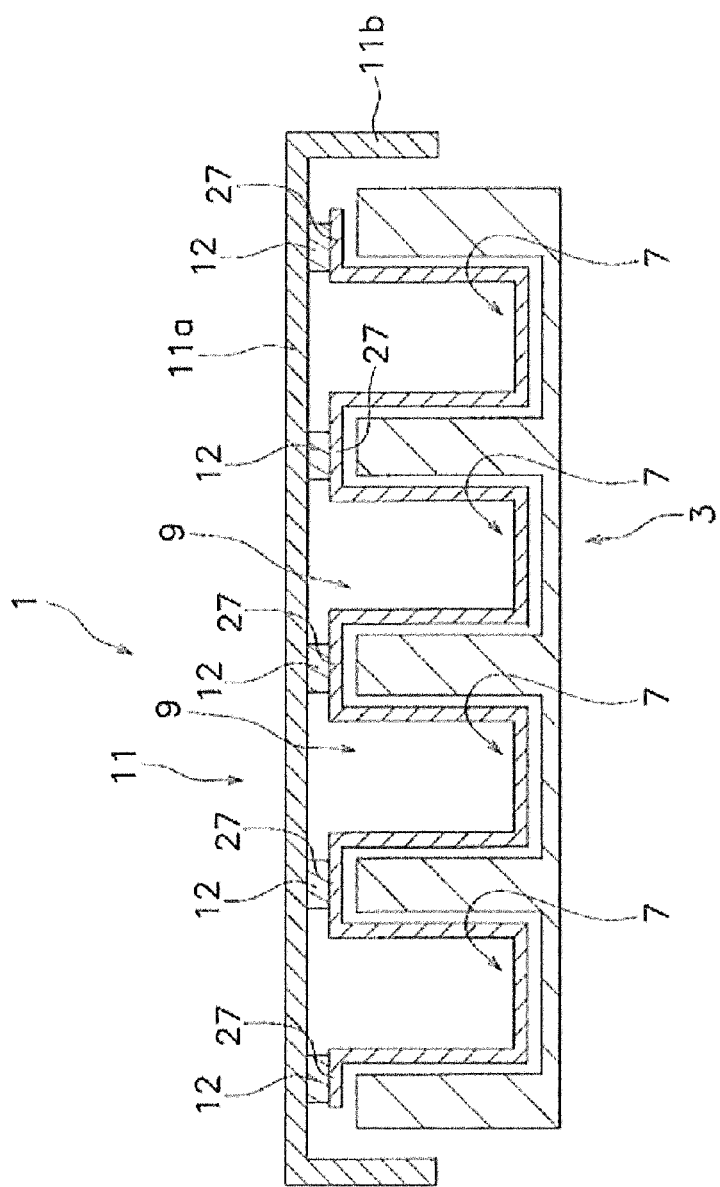
FIG. 28 is a cross-sectional view of the container main body of the cell-culture container according to a twelfth embodiment.

Accordingly, a structure for solving such a problem will now be explained, with reference to FIG. 28. FIG. 28 is a cross-sectional view of the cell-culture container.

As shown in the figure, a cover 11 is disposed above the presser-member-attached plate 5. The cover 11 covers the entire upper side of the presser-member-attached plate 5. The cover 11 includes a flat main body 11a and a tubular part 11b, which extends downward from the outer circumferential edge of the main body 11a. Cushion members 12 are disposed between the main body 11a of the cover 11 and the flange parts 27 of the presser-member-attached plate 5. The cushion members 12 are elastic members such as springs, rubber, and sponges.

The cushion members 12 are compressed between the presser-member-attached plate 5 and the cover 11 and thereby generate an elastic force. Thereby, the presser-member-attached plate 5 is prevented from floating upward and can be fixed inside the container main body 3. Thereby, for example, even in a case of forming spheroids, the gap between the microwells and a mesh can be sufficiently shortened, and thereby a spheroid-fixing effect is obtained.

13. Thirteenth Embodiment

In the twelfth embodiment, the elastic members are compressed only by the intrinsic weight of the cover, but the elastic members may be compressed by some other structure.

Figure 29:
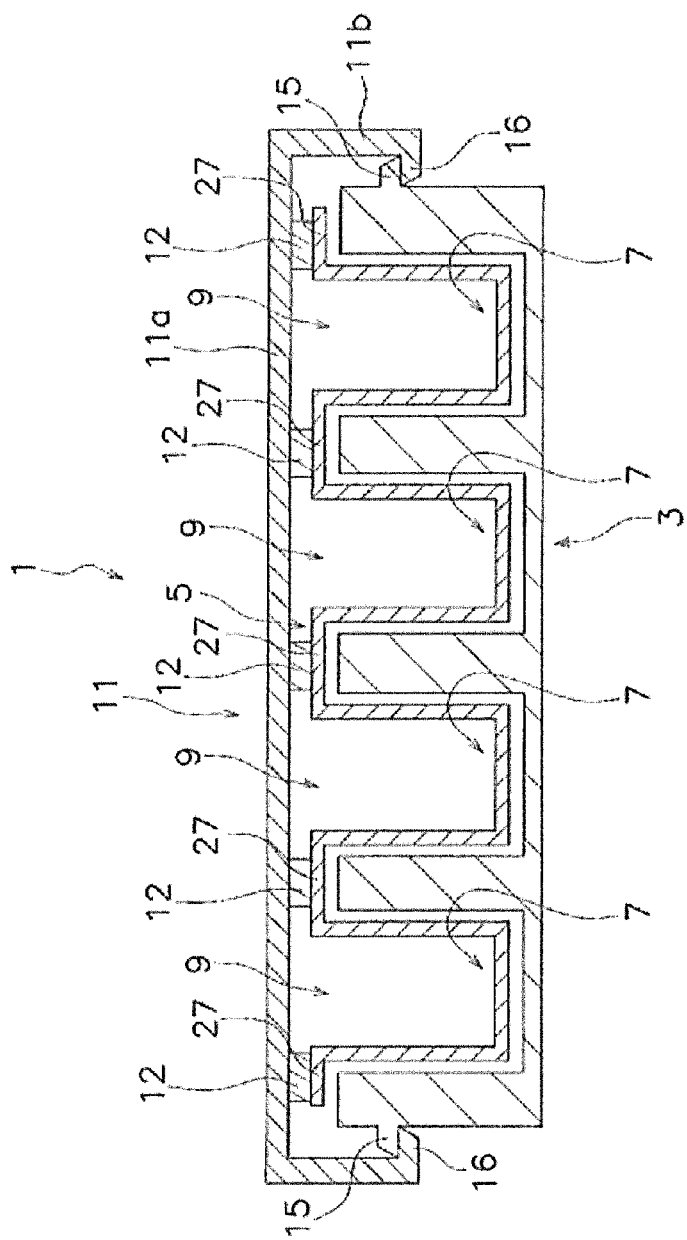
FIG. 29 is a cross-sectional view of the cell-culture container according to a thirteenth embodiment and, along with FIG. 28, according to a fourteenth embodiment.

Accordingly, a structure for solving such a problem will now be explained, with reference to FIG. 29. FIG. 29 is a cross-sectional view of the cell-culture container.

The basic structure is the same as in the twelfth embodiment.

In the present embodiment, a first engaging part 15 is formed on an outer-circumference part of the container main body 3, and furthermore a second engaging part 16 is formed on the tubular part 11b of the cover 11. The first engaging part 15 and the second engaging part 16 engage with one another, and thereby the cover 11 does not separate from the container main body 3.

In the present embodiment, the cushion members 12 are compressed between the presser-member-attached plate 5 and the cover 11, and thereby the elastic force is generated. Thereby, the presser-member-attached plate 5 is prevented from floating and can be fixed inside the container main body 3. Thereby, for example, even in a case wherein spheroids are formed, the gap between the microwell and the mesh can be sufficiently shortened, and thereby the spheroid-fixing effect is obtained.

14. Fourteenth Embodiment

In the twelfth embodiment and the thirteenth embodiment, the presser-member-attached plate 5 is prevented from floating upward by the use of the cover and the cushion members, but it is possible to prevent upward flotation also by other means. For example, the floating due to buoyancy can be prevented by increasing the weight of the presser-member-attached plate 5. Specifically, the intrinsic weight of the presser-member-attached plate 5 can be increased by using a metal material in parts. In addition, a weight can be attached to part of the presser-member-attached plate 5.

15. Fifteenth Embodiment

An embodiment will now be explained wherein positioning structures are provided to both the plurality of presser members and the plurality of recessed parts such that the plurality of presser members smoothly fits into the plurality of the recessed parts.

Figure 30:
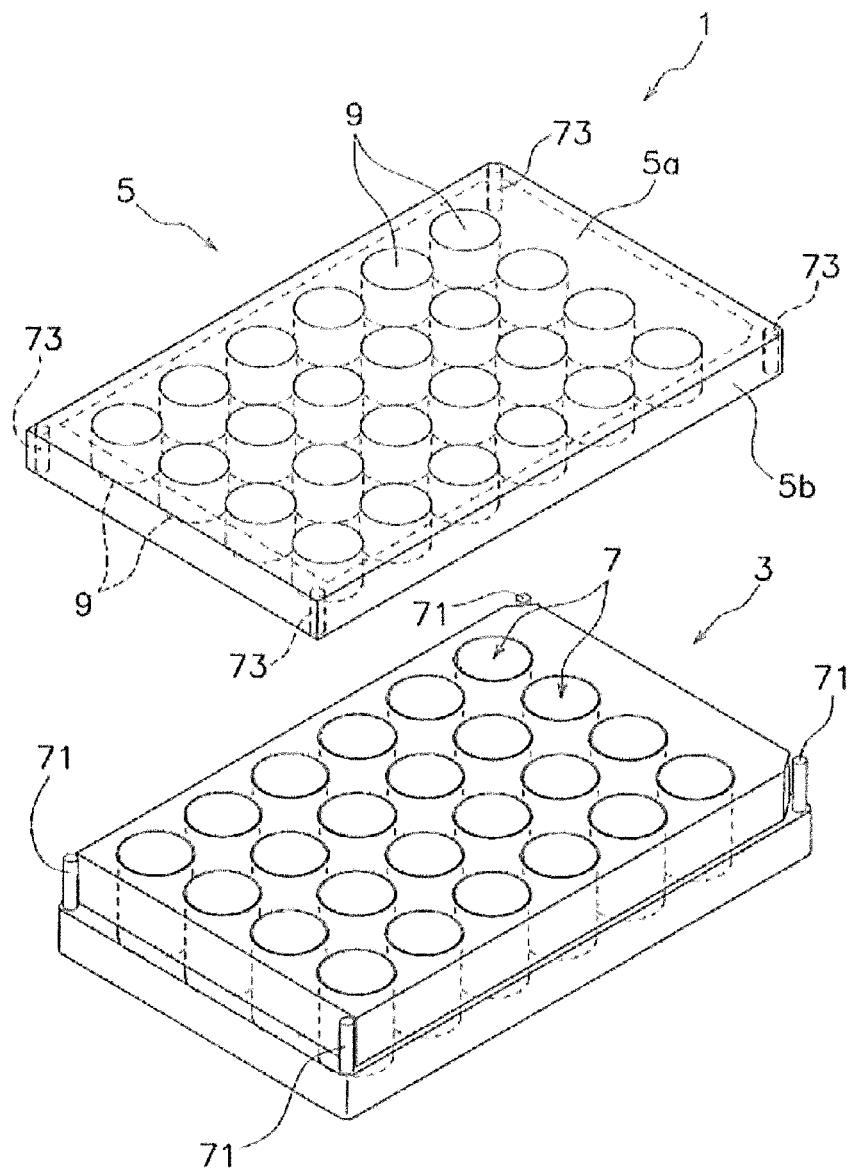
FIG. 30 is an oblique view of the container main body of the cell-culture container according to a fifteenth embodiment.

Such an embodiment will now be explained, with reference to FIG. 30. FIG. 30 is an oblique view of the container main body of the cell-culture container.

Furthermore, the basic structure is the same as in the first through fourteenth embodiments. The explanation below focuses on points of difference.

A plurality of pins 71 are uprightly provided at corners on the upper side of the container main body 3. Specifically, the pins 71 are disposed at the four corners of an outer-side portion of a main-body portion wherein the recessed parts 7 of the container main body 3 are formed.

Holes 73 are formed in the presser-member-attached plate 5 at positions corresponding to the pins 71. Specifically, the holes 73 are formed at the four corners of the frame 5b.

When the presser-member-attached plate 5 is being fitted onto the container main body 3, the presser-member-attached plate 5 and the container main body 3 are positioned by the pins 71 and the holes 73, and thereby the plurality of presser members 9 is fitted smoothly into the recessed parts 7.

Furthermore, the number of the pins and the holes is not limited to the embodiments. Furthermore, the positioning structures of the container main body 3 and the presser-member-attached plate 5 are not limited to pins and holes.

16. Common Features of the Embodiments

The first through fifteenth embodiments described above have the following configurations and functions in common. The culture container (e.g., the cell-culture container 1) includes the container main body (e.g., the container main body 3, and the container main body 103) and the presser member (e.g., the presser members 9, and the presser members 109). The container main body has the recessed parts (e.g., the recessed parts 7, and the recessed part 107) for containing the culture solutions (e.g., the cell-culture solutions C).

Each presser member is a member that is removably fitted onto the upper side of the corresponding recessed part. Each presser member has a lower surface (e.g., the lower surface 23a, the lower surface 41a, the lower surface 45a, the lower surface 49a, the lower surface 53a, the lower surface 57a, the lower surface 61a, and the lower surface 123a) that makes contact with the upper surface of the culture solution in the fitted state, and the bubble-discharge part (e.g., the bubble-discharge part 13, the bubble-discharge part 43, the bubble-discharge part 47, the bubble-discharge part 51, the bubble-discharge part 55, the bubble-discharge part 59, the bubble-discharge part 63, the bubble-discharge part 123b, and the bubble-discharge part 123c) that enables the discharge of bubbles in the culture solution to the exterior.

In the container, the presser members are fitted onto the upper sides of the recessed parts in the state wherein the culture solutions are contained in the recessed parts of the container main body. Thus, the meniscuses are eliminated by the lower surfaces of the presser members making contact with the upper surfaces of the culture solutions. In this state, bubbles in the culture solutions are discharged to the exterior via the bubble-discharge parts of the presser members. As a result, the cells in each culture container can be accurately observed.

17. Other Embodiments

Multiple embodiments of the present invention were explained above, but the present invention is not limited to these embodiments, and various modifications are possible within a scope that does not depart from the gist of the invention. In particular, the embodiments and modified examples written in the present specification can be arbitrarily combined as needed.

The shapes of the recessed part and the presser member in plan view as well as combinations thereof are not limited to the embodiments described above. The number of the recessed parts and the presser members are not limited to the embodiments described above.

The hydrophilization treatment of the lower surface of the presser member may be performed partially or entirely over the lower surface and does not necessarily have to be performed.

If the lower surface of the presser member is configured as a tilted surface, then a portion of or the entire lower surface may be so configured, and the lower surface does not necessarily have to be so configured.

The embodiments explained, as one example of the culture container, a cell-culture container wherein a cell-culture solution is used. However, the culture container according to the present invention can also culture, for example, animal cells, plant cells, bacteria, and microbes.

The present invention can be widely adapted to culture containers that are used in observation via a microscope and that contain a culture solution.

The invention claimed is:

1. A culture container comprising:
a transparent container main body having a recessed part configured to contain a culture solution, the recessed part including a bottom part and a tubular part;
a transparent presser member that is removably fitted onto an upper side of the recessed part, the presser member having
a lower-surface part that makes contact with an upper surface of the culture solution in a fitted state, in which the presser member is fitted to the container main body, to press the upper surface of the culture solution, and
a tubular part having a lower end connected an outer circumferential edge of the lower-surface part and an outer circumferential surface proximately opposing an inner circumferential surface of the tubular part of the recessed part, the tubular part opening upward to directly and entirely expose an upper surface of the lower-surface part outside of the culture container through an opening of the tubular part such that the culture solution is observable from the outside of the culture container through the lower-surface part in the fitted state; and
a bubble-discharge passage that is formed by the outer circumferential surface of the tubular part of the presser member and the inner circumferential surface of the tubular part of the recessed part, the outer circumferential surface of the tubular part of the presser member facing the inner circumferential surface of the tubular part of the recessed part, the bubble-discharge passage enabling discharge of bubbles in the culture solution to an exterior.

2. The culture container according to claim 1, wherein the lower-surface part of the presser member has a planar end surface that extends horizontally.

3. The culture container according to claim 2, wherein the lower-surface part of the presser member is subject, at least partially, to a hydrophilization treatment.

4. The culture container according to claim 3, wherein the presser member further includes a liquid-supply passage, and
the liquid-supply passage is used to inject a liquid into the culture solution so as to move bubbles in the culture solution toward the bubble-discharge passage.

5. The culture container according to claim 2, wherein the presser member further includes a liquid-supply passage, and
the liquid-supply passage is used to inject a liquid into the culture solution so as to move bubbles in the culture solution toward the bubble-discharge passage.

6. The culture container according to claim 1, wherein the lower-surface part of the presser member is subject, at least partially, to a hydrophilization treatment.

7. The culture container according to claim 6, wherein the presser member further includes a liquid-supply passage, and
the liquid-supply passage is used to inject a liquid into the culture solution so as to move bubbles in the culture solution toward the bubble-discharge passage.

8. The culture container according to claim 1, wherein the presser member further includes a liquid-supply passage, and
the liquid-supply passage is used to inject a liquid into the culture solution so as to move bubbles in the culture solution toward the bubble-discharge passage.

* * * * *